United States Patent [19]

Downie

[11] Patent Number: 5,001,938
[45] Date of Patent: Mar. 26, 1991

[54] SAMPLING SYSTEM

[76] Inventor: Ronald A. Downie, 30,000 Sand Canyon Rd., Suite 6, Santa Clarita, Calif. 91351

[21] Appl. No.: 404,105

[22] Filed: Sep. 7, 1989

[51] Int. Cl.⁵ .................................................. G01N 1/20
[52] U.S. Cl. ................................. 73/864.34; 73/866.5; 356/128; 250/431; 250/576
[58] Field of Search ............ 73/864.73, 864.34, 863.61, 73/864.74, 864.35, 866.5, 864.33; 356/128–137; 250/431, 573, 576; 162/49, 198, 263

[56] References Cited

U.S. PATENT DOCUMENTS

| | | | |
|---|---|---|---|
| 1,827,658 | 10/1931 | Johnsen | 162/49 |
| 2,912,858 | 11/1959 | Fuller | 250/576 X |
| 3,498,719 | 3/1970 | Wing et al. | 162/198 X |
| 3,778,165 | 12/1973 | Grubb et al. | 356/128 |
| 3,812,482 | 5/1974 | Clark | 250/573 X |
| 4,034,219 | 7/1977 | Louden et al. | 250/431 X |
| 4,094,187 | 6/1978 | Navarre, Jr. | 73/864.34 X |
| 4,115,229 | 9/1978 | Capone | 73/863.61 X |
| 4,135,382 | 1/1929 | Capone | 73/23 |
| 4,215,565 | 8/1980 | Zanker | 73/863.61 X |
| 4,375,170 | 3/1983 | Sperry, III et al. | 73/866.5 |

FOREIGN PATENT DOCUMENTS

| | | | |
|---|---|---|---|
| 2435472 | 2/1982 | Fed. Rep. of Germany | 73/863.61 |
| 3440729 | 5/1985 | Fed. Rep. of Germany | 73/864.73 |

Primary Examiner—Tom Noland
Attorney, Agent, or Firm—Kelly Bauersfeld & Lowry

[57] ABSTRACT

An improved sampling system is provided for on-line monitoring of a liquid such as a process liquor in a paper mill or the like. The sampling system includes, in general terms, an improved sampling probe for circulating process liquor from a process tank or the like to a sensor device such as a refractometer for monitoring of selected parameters. The sampling probe includes intake and return conduits having ends nested within an open-ended probe housing disposed within the process tank, such that the intake and return conduit ends are shielded from direct contact with large particulate settling within the tank. The intake and return conduit ends are further arranged for intersection of liquor flow streams associated therewith at a position inset within the probe housing to generate turbulence which tends to sweep large particulate away from the probe while maintaining smaller particulate in suspension to avoid probe clogging. In addition, the sensor device includes a brush unit for preventing accumulation of particulate which could otherwise interfere with the monitoring process.

24 Claims, 2 Drawing Sheets

SAMPLING SYSTEM

BACKGROUND OF THE INVENTION

This invention relates generally to devices and systems for monitoring parameters of a selected fluid, particularly such as a process liquor used in manufacturing operations such as a paper mill or the like. More specifically, this invention relates to a sampling system for on-line monitoring of one or more fluid parameters of a process liquor, wherein the improved sampling system is designed for substantially continuous operation with a process liquor laden with a significant proportion of particulate material.

In many industrial operations, process fluids are used in the course of manufacture and/or treatment of industrial products. Such process fluids in form are often referred to as process liquors, frequently have a specific formulation which must be maintained within prescribed range limits for the industrial process to proceed in an efficient and economical manner. Accordingly, monitoring devices and systems are required to test one or more selected process liquor parameters on a periodic or continuous basis, thereby permitting appropriate remedial adjustment of the liquor formulation on an as-needed basis.

As one example, paper mills utilize a caustic process liquor to digest wood chips and/or other cellulosic material to produce pulp which is subsequently processed to form paper of different types and grades. The caustic process liquor is recovered from a digester unit for chemical recovery or regeneration and subsequent re-supply to the digester unit. The chemical recovery process involves a sequence of liquor treatment steps utilizing equipment such as boilers, dissolving tanks, clarifier tanks, etc., with frequent and/or continuous analysis of liquor parameters such as alkalinity being extremely desirable to insure that the process proceeds in an efficient, economical and safe manner. Efficient process performance can be of critical importance to insure a substantially constant supply of regenerated process liquor to the digester unit, in spite of flow surges and other process parameter variations which often occur.

In the context of paper mill liquor recovery processes, however, accurate monitoring of liquor parameters such as alkalinity is significantly hampered by substantial quantities of particulate and scale present in the process liquor. More particularly, monitoring devices such as pressure cell transmitter tubes have been installed into the process liquor to obtain density readings which can be correlated with alkalinity. Such pressure cell tubes unfortunately encounter frequent clogging with particulate and scaling. Other proposed monitoring devices having included radiation gauges and conductivity monitors which avoid tubing and related clogging problems, but otherwise encounter scale buildup resulting in inaccurate readings. Accordingly, to obtain accurate alkalinity measurements, it has been necessary to remove liquor samples from the process stream at periodic intervals for separate laboratory analysis by titration or optical refractometer techniques. Such separate analysis is unfortunately inadequate to permit rapid process cycle adjustment to accommodate potentially rapidly changing process conditions.

There exists, therefore, a significant need for improvements in fluid sampling systems, particularly with respect to providing on-line and substantially continuous liquor monitoring capability irrespective of the presence of substantial particulate quantities in process liquor. The present invention fulfills these needs and provides further related advantages.

SUMMARY OF THE INVENTION

In accordance with the invention, an improved fluid sampling system is provided for monitoring at least one selected parameter of a process fluid particularly such as a caustic process liquor in a paper mill or the like. The sampling system includes an improved sampling probe for tapping a small portion of the process liquor from a process tank or the like for flow to a sensor device, followed by recirculation of the process liquor to the tank, all in a manner avoiding clogging of the probe by particulate and/or scaling. The sampling system further includes a sensor unit having a sensor and means for cleaning accumulated particulate and/or scale from the sensor to avoid interference with sensor readings.

In the preferred form, the sampling probe includes an intake conduit and a return conduit having ends disposed within the process fluid such as within a process tank or other fluid flow streams such as a pipeline. The intake and return conduits function to draw a stream of the process fluid for substantially continuous flow through the sensor unit for analysis and recirculation to the process tank or the like. These conduits conveniently define stainless steel and/or Teflon coated flow surfaces, and are associated with a pump of similar construction for process liquor circulation substantially without scale formation.

Within the process liquor tank or the like, the ends of the intake and return conduits are nested within an open-ended probe housing oriented to shield the conduits from direct contact with particulate settling within the tank. Moreover, the ends of the intake and return conduits are arranged for intersection of respective intake and return flow streams at a position inset slightly into the probe housing. The arrangement results in substantial process liquor turbulence at a location adjacent to ends of the intake and return conduits, wherein this turbulence beneficially sweeps larger particulate away from the conduit ends and maintains smaller particulate in suspension to minimize or eliminate clogging problems. Circulation flow through the conduits is periodically reversed to further reduce clogging problems.

The sensor unit preferably comprises the sensor such as a refractometer for optically analyzing the process liquor through a sight window such as a prism or the like. The cleaning means comprises a cleaning brush operated intermittently or continuously to sweep particulate and/or scale from the sight window. The brush is rotatably carried on a driven shaft coupled to a drive motor through sealed drive means such as a hermetically sealed magnetic drive coupling or the like. The driven shaft and associated drive coupling components are periodically or continuously flushed with water or other selected flush fluid to avoid binding attributable to particulate and/or scale from the process liquor.

Other features and advantages of the invention will become more apparent from the following detailed description, taken in conjunction with the accompanying drawings which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENT

Figure 1:
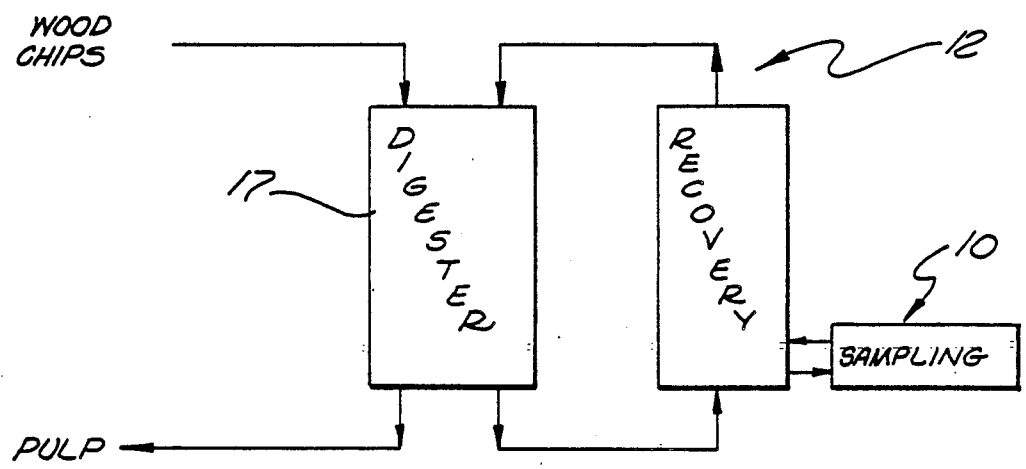
FIG. 1 is a schematic diagram illustrating portions of a paper mill production process utilizing a process liquor and the improved sampling system embodying the novel features of the invention.

As shown in the exemplary drawings, an improved fluid sampling system is provided for use in monitoring a process fluid, particularly such as a process liquor of the type used in a paper mill or the like. The improved sampling system is referred to generally by the reference numeral 10 in FIGS. 1 and 2, and may be used in the process liquor recovery cycle 12 for a paper mill, as depicted in FIG. 1, or in other types of industrial processes or the like requiring monitoring of at least one fluid parameter. The sampling system 10 of the present invention includes an improved sampling probe 14 (FIG. 2) for use in circulation of the process liquor to a sensor unit 16, wherein both the sampling probe 14 and the sensor unit 16 are designed for substantially continuous on-line operation without clogging by particulate and the like present within the sampled process liquor.

FIG. 1 illustrates a portion of a paper mill production process or the like, wherein wood chips and/or other cellulosic fiber material is digested by a caustic process liquor in a digester 17 to produce pulp utilized in the manufacture of various paper products. The digester 17 also produces an outflow of spent process liquor, which is recycled to the recovery cycle 12 for regeneration and re-supply to the digester. This recovery cycle 12 generally includes a sequence of process stages known in the art, such as an evaporator, a boiler, a dissolving tank, slaker and appropriate clarifier tanks (not shown in detail in FIG. 1) for recausticizing the process liquor to a controlled density for efficient and economical conversion of the wood material to pulp form. The liquid sampling systems 10 of the present invention is particularly designed for monitoring the process liquor throughout the recovery cycle to insure a substantially uniform supply of process liquor of controlled alkalinity to the digester, notwithstanding flow surges and other processing variables which commonly occur. In this regard, the sampling system 10 is primarily intended for sampling the process liquor at the least stable point of the recovery cycle 12 by sampling the process liquor 18 within a dissolving tank 20 as shown in FIG. 2, although the sampling system can be used additionally to sample the process liquor at other locations in the process system, such as in selected flow lines or clarifier tanks, etc.

Moreover, although the invention is shown and described with reference to process liquor monitoring in a paper mill, it will be understood that the invention is applicable for monitoring other types of process fluids or process liquors and the like.

Figure 2:
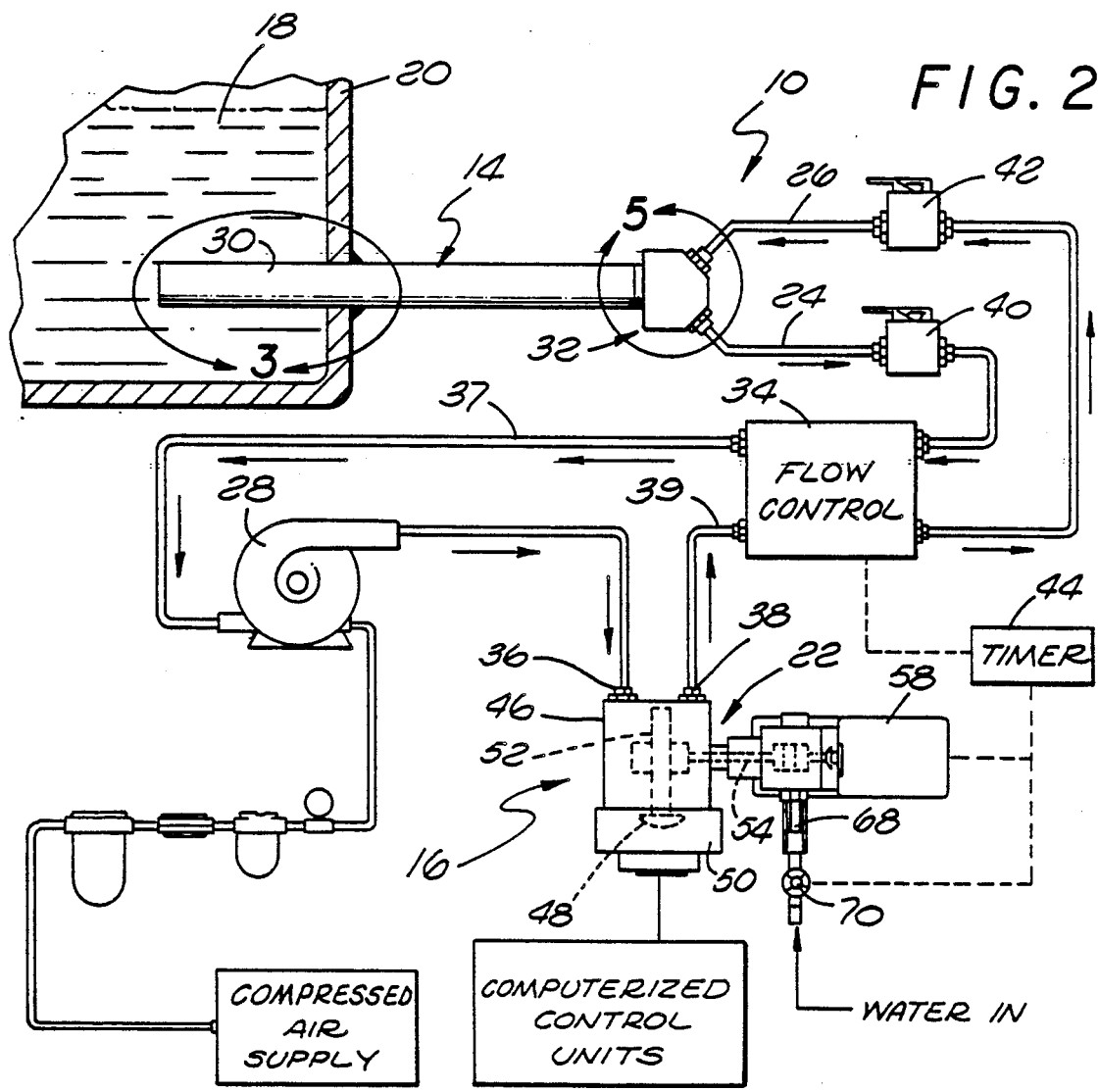
FIG. 2 is an enlarged fragmented and somewhat schematic diagram depicting the improved liquid sampling system embodying the novel features of the invention.

The liquid sampling system 10 is depicted generally in FIG. 2 to include the sampling probe 14 extending into direct contact with the process liquor 18 contained within the dissolving tank 20. The sampling probe 14 is designed for circulating a relatively small proportion of the process liquor 18 to the sensor unit 16 for analysis, such as optical analysis to obtain a density reading which can be directly correlated with alkalinity level. The geometry of the sampling probe 14 prevents intake of relatively large particulate which is typically present in the process liquor, and further maintains relatively smaller particulate in suspension to avoid clogging of sampling system flow lines. In addition, the sensor unit 16 incorporates cleaning means 22 for preventing undesired accumulation of particulate and/or scale, and resultant clogging potential.

Figure 3:
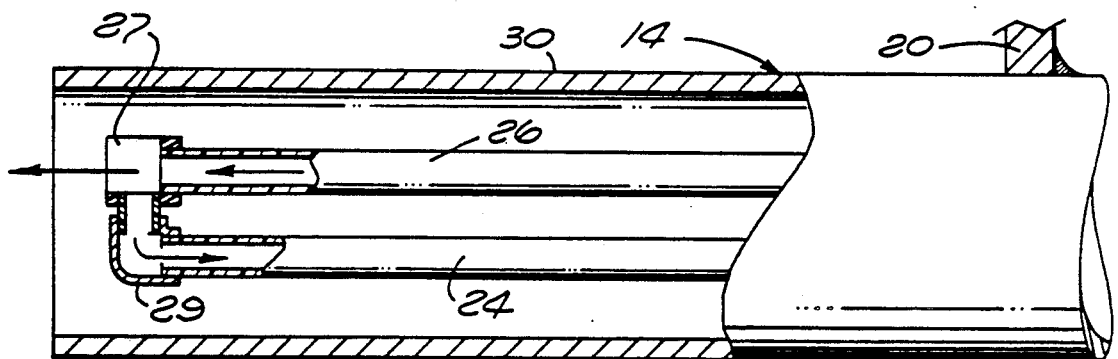
FIG. 3 is an enlarged fragmented front elevation view of an improved sampling probe, corresponding generally with the the encircled region 3 of FIG. 2.
Figure 4:
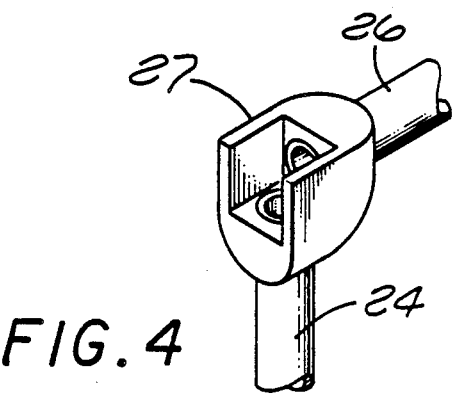
FIG. 4 is a fragmented perspective view illustrating a preferred geometry for intake and return conduits of the sampling probe.

More specifically, as shown best in FIGS. 3 and 4, the sampling probe 14 comprises an intake conduit 24 and a return conduit 26 extending into direct contact with the process fluid 18, such as by sealed passage through a wall of the dissolving tank 20. The intake and return conduits 24 and 26 respectively provide a first flow path through which the process liquor is drawn by a pump 28 or the like for flow to the sensor unit 16, and a second flow path through which the process liquor is recycled from the sensor unit 16 to the tank 20. These conduits 24 and 26 conveniently comprise substantially constant diameter tubing formed from or coated with a Teflon film or the like to permit process liquor flow substantially without scale formation which could otherwise clog the conduits. In this regard, it is desirable to maximize the flow surfaces formed from a Teflon or Teflon coated material. Within the tank 20, the ends of the intake and return conduits 24 and 26 are nested in an inset position within an open-ended housing 27, seated within a tubular probe housing 30 which is oriented generally horizontally to shield the end of the conduits 24 and 26 from relatively large particulate matter settling within the tank. Alternately, the probe housing 30 may be oriented to open downwardly, if desired.

The ends of the intake and return conduits 24 and 26 are supported by the fitting 27 in closely adjacent positions oriented for intersection of their respective flow streams at a position inset slightly from the open end of the probe housing 30. FIG. 3 depicts such intersection with the return conduit 26 extending generally linearly for returning recycled process liquor to the tank, and with the intake conduit 24 intersecting the recycled flow stream at a right angle. With this geometry, the return flow tends to sweep any large particulate at or near the open end of the probe housing 30 in a direction away from the intake conduit 24. In addition, the intersecting return and intake flows generate substantial turbulence at the entrance of the intake conduit, such that smaller particulate is maintained in suspension. The process liquor with any entrained small particulate may thus be pumped through the conduits 24 and 26 without significant risks of clogging. Alternately, other intersecting conduit geometries can be used, such as an arrangement with the flow streams intersecting at other angles. Moreover, a right angle fitting 29 can be installed along the length of the conduit 24 to insure a right angle bend without crimping.

Figure 5:
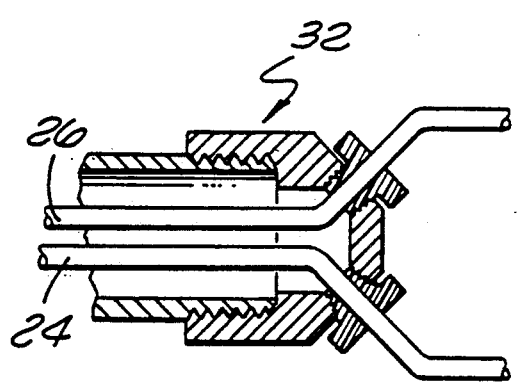
FIG. 5 is an enlarged fragmented vertical section of a Y-junction fitting corresponding generally with the encircled region 5 of FIG. 2.

The intake and return conduits 24 and 26 extend through the probe housing 30 to the exterior of the tank 20 to a Y-junction fitting 32, as viewed in FIGS. 2 and 5. From this fitting, the conduits 24 and 26 extend respectively to a flow control module 34, and further to intake and return ports 36 and 38 on the sensor unit 16 via a pair of supply conduits 37 and 39. Separate shut-off valves 40 and 42, such as Teflon ball valves, are conveniently provided to permit manual shut-off, and the pump 28 is normally connected in-line with the supply conduit 37, with an air driven pump being depicted in the illustrative drawings. The flow control module 34 includes appropriate solenoid operated valves or the like for reversing the direction of process liquor flow between the module 34 and the sensor unit 16, in response to programmed inputs from a timer 44, as will be described in more detail.

The sensor unit 16 comprises a main flow block 46 for flow-through passage of the process liquor between the supply conduits 37 and 39. Sensor means is mounted along the flow path to permit monitoring of the process liquor. In a preferred form, this sensor means comprises a sensor head 50 which may contain an optical sensor for viewing the process fluid through a sight window 48. As depicted in FIG. 2, in connection with a paper mill process, the sight window 48 comprises a sapphire prism, and the sensor head 50 comprises a process refractometer such as are available from several instrument manufacturers. Such refractometer provides optical density readings which can be coupled to appropriate computer units or the like for correlating the density readings with liquor alkalinity level.

Figure 6:
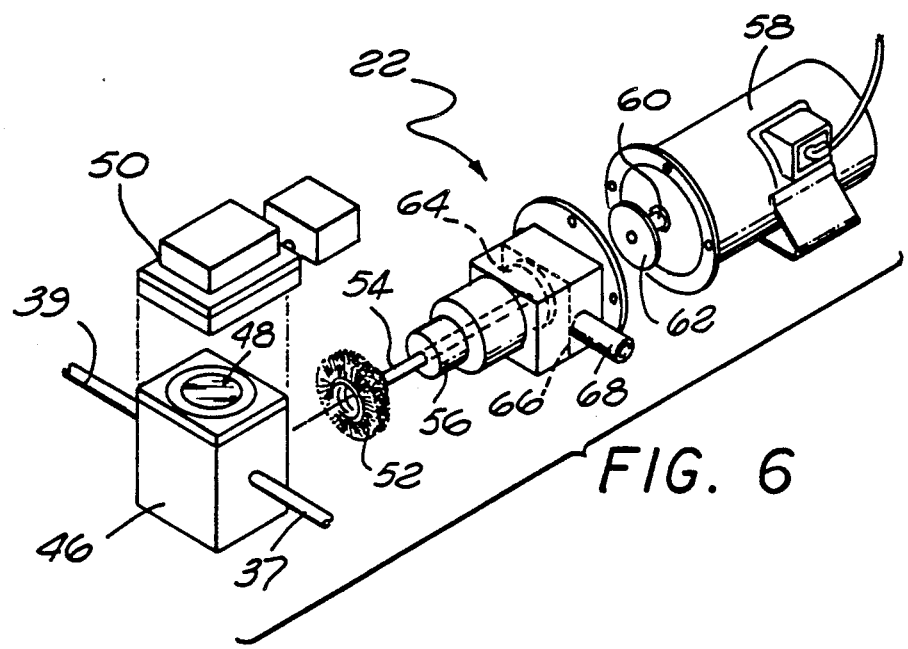
FIG. 6 is an exploded perspective view depicting an improved sensor unit.

In accordance with one primary aspect of the invention, the flow block 46 of the sensor unit 16 incorporates the cleaning means 22 to prevent obscuring the sight window 48 with particulate or scale, etc. The cleaning means 22 comprises, as shown in FIG. 6, an impeller brush 52 carried within the flow block for periodic or continuous rotational driving to sweep particulate and the like from the sight window. The brush 52 is supported by a driven shaft 54 rotatable within suitable bearings 56. A drive motor 58 such as a variable speed motor has a drive shaft 60 coupled to the driven shaft 54 to rotate the brush. However, to avoid contamination of the motor 58 and the related drive shaft 60 with caustic process liquor, the drive and driven shafts 60 and 54 respectively carried drive magnets 62 and 64 in coupled relation through a hermetically sealed barrier 66.

Hydraulic flush means is also included to insure reliable operation of the cleaning brush 52. More particularly, a water flush line 68 or the like is controlled by operation of a valve 70 (FIG. 2) to provide flush water which flows past the drive magnet 64 and the driven shaft 54 within the bearings 56 to flush contaminants from the sealed driven area back into the circulation flow stream. This supply of flush water is desirably regulated by the timer 44 which also desirably operates the motor 58 at concurrent selected intervals.

Accordingly, the liquid sampling system 10 of the invention circulates the process liquor continuously through the conduits 24 and 26 and the related supply conduits 37 and 39 to the sensor unit 16 for analysis. The probe 14 has a geometry which avoids clogs due to intake of large particulate. The timer 44 periodically operates the flow control module 34 to reverse the direction of flow through the supply conduits for purposes of further minimizing risk of clogging. This timer 44 additionally operates the brush motor 58 and the hydraulic flush valve 70 which cleanses moving parts of the cleaning apparatus to prevent particulate and scale buildup. Process liquor readings can be taken by the sensor head 50 on a continuous or frequent intermittent basis. Conveniently, all of the flow conduits and related valves in the system can be constructed from stainless steel or Teflon or Teflon coated material to avoid undersired scale accumulation.

A variety of further modifications and improvements of the improved liquid sampling system will be apparent to those skilled in the art. For example, it will be understood that the sensor unit 16 can be adapted for monitoring a process fluid contained within any type of tank or flow pipeline or the like. Accordingly, no limitation on the invention is intended by way of the foregoing description and the accompanying drawings, except as set forth in the appended claims.

What is claimed is:

1. A sampling system for monitoring at least one parameter of a process liquor or the like, said sampling system comprising:

a sampling probe having a probe housing extending into the process liquor and defining an open housing end to permit flow of the process liquor into said probe housing, and an intake conduit and a return conduit having open ends disposed within said probe housing for angular intersection of process liquor streams associated with said intake and return conduits at a position slightly inset from the open end of said probe housing;

a sensor unit including a flow block for flow through passage of the process liquor and means for monitoring at least one parameter of the process liquor within said flow block; and means for circulating the process liquor to said flow block through said intake conduit and for returning the process liquor to said probe through said return conduit.

2. The sampling system of claim 1 wherein said intake and return conduits are interconnected for intersection of process liquor streams associated therewith.

3. The sampling system of claim 1 wherein said circulating means comprises a pump.

4. The sampling system of claim 1 wherein said monitoring means comprises an optical detector, and further wherein said flow block defines a sight window to permit viewing of the process liquor within said flow block by said optical detector.

5. The sampling system of claim 4 wherein said optical detector comprises a refractometer.

6. The sampling system of claim 1 further including cleaning means within said flow block for cleaning particulate material from said sensor unit.

7. A sampling system for monitoring at least one parameter of a process fluid or the like, said sampling system comprising:

a sampling probe having a probe housing extending into the process fluid and defining an open housing end to permit flow of the process fluid into said probe housing, and an intake conduit and a return conduit having ends disposed within said probe housing at a position at least slightly inset from the open end of said probe housing;

a sensor unit including a flow block for flow through passage of the process fluid and means for monitoring at least one parameter of the process fluid within said flow block;

means for circulating the process fluid to said flow block through said intake conduit and for returning the process fluid to said probe through said return conduit, said circulating means comprising a pump and further including a pair of supply conduits coupled to said flow block of said sensor unit, and means for connecting said supply conduits respectively to said intake and return conduits, said connecting means including reverse flow means for periodically reversing the connection of said supply conduits to said intake and return conduits for reversing the direction of process fluid flow through said supply conduits and said flow block.

8. A sampling system for monitoring at least one parameter of a process fluid or the like, said sampling system comprising:

a sampling probe having a probe housing extending into the process fluid and defining an open housing end to permit flow of the process fluid into said probe housing, and an intake conduit and a return conduit having ends disposed within said probe housing at a position at least slightly inset from the open end of said probe housing;

a sensor unit including a flow block for flow through passage of the process fluid and means for monitoring at least one parameter of the process fluid within said flow block; and means for circulating the process fluid to said flow block through said intake conduit and for returning the process fluid to said probe through said return conduit; and cleaning means within said flow block for cleaning particulate material from said sensor unit, said cleaning means comprising a brush, and further including drive means for moving said brush to clean said sensor unit.

9. The sampling system of claim 8 wherein said drive means comprises a drive motor having a drive shaft, a driven shaft carrying said brush, hermetically sealed coupling means interconnecting said drive and driven shafts, and flush means for flushing particulate from said coupling means into said flow block.

10. The sampling system of claim 9 wherein said flush means comprises a water flush supply, a valve for opening said water flush supply to flow past said driven shaft into said flow block, and timer means for intermittently opening said valve.

11. The sampling system of claim 9 wherein said sealed coupling means comprises a magnetic coupling.

12. A sampling system for monitoring at least one parameter of a process fluid or the like, said sampling system comprising;

a sampling probe having a probe housing extending into the process fluid and defining an open housing end to permit flow of the process fluid into said probe housing, and an intake conduit and a return conduit having ends disposed within said probe housing at a position at least slightly inset from the open end of said probe housing, said intake and return conduits being mounted within said probe housing for intersection of process fluid streams associated with said intake and return conduits at a position at least slightly inset within said probe housing;

a sensor unit including a flow block for flow through passage of the process fluid and means for monitoring at least one parameter of the process fluid within said flow block;

means for circulating the process fluid to said flow block through said intake conduit and for returning the process fluid to said probe through said return conduit; and cleaning means for cleaning particulate material from said sensor, said cleaning means comprising a brush, a drive motor having a drive shaft, a driven shaft carrying said brush, hermetically sealed coupling means interconnecting said drive and driven shafts, and flush means for flushing particulate from said coupling means into said flow block.

13. The sampling system of claim 12 wherein said flush means comprises a water flush supply, a valve for opening said water flush supply to flow past said driven shaft into said flow block, and timer means for intermittently opening said valve.

14. The sampling system of claim 12 wherein said sealed coupling means comprises a magnetic coupling.

15. The sampling system of claim 12 wherein said intake and return conduits are interconnected for intersection of process fluid streams associated therewith.

16. The sampling system of claim 12 wherein said circulating means comprises a pump.

17. The sampling system of claim 12 wherein said probe housing is oriented to substantially prevent entry thereinto of particulate material settling within the process fluid.

18. A sampling system for monitoring at least one parameter of a process fluid or the like, said sampling system comprising;

a sampling probe having a probe housing extending into the process fluid and defining an open housing end to permit flow of the process fluid into said probe housing, and an intake conduit and a return conduit having ends disposed within said probe housing at a position at least slightly inset from the open end of said probe housing, said intake and return conduits being mounted within said probe housing for intersection of process fluid streams associated with said intake and return conduits at a position at least slightly inset within said probe housing.

a sensor unit including a flow block for flow through passage of the process fluid and means for monitoring at least one parameter of the process fluid within said flow block;

means for circulating the process fluid to said flow block through said intake conduit and for returning the process fluid to said probe through said return conduit; and cleaning means for cleaning particulate material from said sensor;

said circulating means comprising a pump and further including a pair of supply conduits coupled to said flow block of said sensor unit, and means for connecting said supply conduits respectively to said intake and return conduits, said connecting means including reverse flow means for periodically reversing the connection of said supply conduits to said intake and return conduits for reversing the direction of process fluid flow through said supply conduits and said flow block.

19. A sampling probe for drawing and returning a sample of process liquor or the like for analysis, said sampling probe comprising;

a probe housing extending into the process liquor and having an open end oriented to substantially prevent entry thereinto of particulate material settling within the process liquor;

an intake conduit and a return conduit mounted within said probe housing and having adjacent ends disposed at a position slightly inset from said probe housing open end and oriented for substantial angular intersection of process liquor streams associated with said intake and return conduits.

20. A sensor unit for monitoring at least one parameter of a process fluid or the like, said sensor unit comprising;

a flow block for flow through passage of at least a portion of the process fluid to be monitored;

a sensor head including a sensor device for monitoring the process fluid within said flow block, said sensor device comprising a refractometer, and a sight window formed on said flow block; and means for cleaning particulate material from said sensor device, said cleaning means comprising a brush within said flow block.

21. The sensor unit of claim 20 wherein said cleaning means further includes a driven shaft carrying said brush, hermetically sealed coupling means interconnecting said drive and driven shafts, and flush means for flushing particulate from said coupling means into said flow block.

22. The sensor unit of claim 21 wherein said flush means comprises a water flush supply, a valve for opening said water flush supply to flow past said driven shaft into said flow block, and timer means for intermittently opening said valve.

23. The sensor unit of claim 22 wherein said sealed coupling means comprises a magnetic coupling.

24. The sensor unit of claim 20 further including means for automatically and intermittently operating said cleaning means.

* * * * *